United States Patent [19]

Blatt et al.

[11] Patent Number: 5,980,884
[45] Date of Patent: Nov. 9, 1999

[54] METHODS FOR RETREATMENT OF PATIENTS AFFLICTED WITH HEPATITIS C USING CONSENSUS INTERFERON

[75] Inventors: Larry Blatt, Boulder, Colo.; Michael Klein, Thousand Oaks, Calif.

[73] Assignee: Amgen, Inc., Thousand Oaks, Calif.

[21] Appl. No.: 08/595,440

[22] Filed: Feb. 5, 1996

[51] Int. Cl.$^6$ .......................... A61K 38/21; A61K 38/19; C07K 14/555; C07K 14/56
[52] U.S. Cl. ...................... 424/85.4; 424/85.5; 424/85.6; 424/85.7; 530/351
[58] Field of Search ................................ 424/85.4, 85.5, 424/85.6, 85.7; 530/351

[56] References Cited

U.S. PATENT DOCUMENTS

| | | | |
|---|---|---|---|
| 4,695,623 | 9/1987 | Stabinsky | 530/351 |
| 4,897,471 | 1/1990 | Stabinsky. | |
| 5,372,808 | 12/1994 | Blatt et al.. | |

FOREIGN PATENT DOCUMENTS

WO 93 21229  10/1993  WIPO .

OTHER PUBLICATIONS

Arase et al., "Interferon Retreatment of Nonresponders with HCV–RNA–Positive Chronic Hepatitis C", *J. Gastroenterol.*, 29: 299–304 (1994).

Marcellin et al., "Retreatment with Recombinant Interferon–alpha in Patients with Chronic Hepatitis C", *Journal of Infectious Diseases*, 167:780–781 (1993).

Marriott et al., "Retreatment of Chronic Hepatitis C with Interferon–alpha", *Journal of Infectious Diseases*, 166:1200–1201 (1992).

Schvarcz et al, "Interferon alpha–2b Treatment of Chronic Posttransfusion non–A, non–B/C Hepatitis: Long term Outcome and Effect of Increased Interferon Doses in Non–Responders", *Scand J. Infect Dis*, 23: 413–420 (1991).

Toyoda et al, "Retreatement of Chronic Hepatitis C with Interferon", *American Journal of Gastroenterology*, 89(9): 1453–1457 (1994).

Welland et al, "Serum HCV RNA Levels in Patients with Chronic Hepatitis C Given a Second Course of Interferon alpha–2b Treatment after Relapse Following Initial Treatment", *Scand J. Infect Dis*, 25:25–30 (1993).

Iino et al. Intervirology 37:87–100, 1994.

Tong et al (A) Gastroenterology 108 (4 Suppl.):A1188, 1995 top right.

Marcellin et al. (AB) J. Infectious Dis. 167:780–781, 1993.

Bresci et al. J. Viral Hepatitis v2, N3:155–158, 1995.

Ozes et al. J. Interferon Res. 12:55–59, 1992.

Tong et al. (B) Gastroenterology 108 (4 Suppl.):A1188, top left Abstract, 1995.

Tong et al. (C) Hepatology 18 (part 4):150A, abstract No. 376, 1993.

M.J. Tong et al., "Retreatment of Patients with Chronic Hepatitis C Virus Infection with Consensus Interferon Results of a Maintenance Study", Gastroenterology, vol. 108, No. 4, Suppl., Apr. 1995, New York, N.Y., U.S.

M.J. Tong, et al., "Long–Term Follow–Up of Patients Treated with Consensus Interferon", Gastroenterology, vol. 108, No. 4 Suppl., Apr. 1995, New York, N.Y., U.S.

M.J. Tong, et al., "Treatment of Patients with Chronic HCV Infection with a Novel Type–1 Interferon, Consensus Interferon", Hepatology, vol. 18, No. 4 Part 2, Oct. 1993, Baltimore, PA, U.S.

D.M. Jensen, et al., "Treatment of High Viral Titer Chronic HCV Patients with Consensus Interferon (CIFN) Results in a Significantly Greater Number of Sustained HCV RNA Reponsders as Compared to Treatment with Interferon Alpha–2b", Hepatology, vol. 24, No. 4 Part 2, Oct. 1996, Baltimore, PA, U.S.

Infergen (Interferon alfacon–1); (Oct. 1997).

Alberti, et al. "Therapy of Hepatitis C: Re–Treatment with Alpha Interferon"; Hepatology vol. 26, No. 3 (Sep. 1997) pp. 137–142.

Heathcote, et al. "Re–treatment of Chronic Hepatitis C with Consensus Interferon"; Hepatology (Apr. 1998) pp. 1136–1143.

*Primary Examiner*—F C Eisenschenk
*Assistant Examiner*—Mary K Zeman
*Attorney, Agent, or Firm*—Craig A. Crandall; Ron K. Levy; Steven M. Odre

[57] ABSTRACT

Methods for the retreatment, using a therapeutically effective amount of interferon consensus, of patients with HCV who exhibit serum ALT values above the upper limit of normal after previous treatment with interferon.

7 Claims, No Drawings

METHODS FOR RETREATMENT OF PATIENTS AFFLICTED WITH HEPATITIS C USING CONSENSUS INTERFERON

The present invention relates to methods of retreatment, using consensus interferon (IFN-con), of patients suffering from Hepatitis C virus (HCV) who failed to respond to the initial course of treatment with interferon, or who, following cessation of interferon therapy, suffered relapse.

BACKGROUND OF THE INVENTION

Hepatitis C virus (HCV) is one of five viral agents known to cause viral hepatitis. HCV is a small RNA virus that resembles the flavi- or pestiviruses in its nucleotide sequence and genomic structure; Houghton et al., *Hepatology,* 14:381, 1991. Patients actively infected with HCV have HCV-RNA in blood which can be detected using sensitive assays employing reverse transcription followed by polymerase chain reaction amplification (RT-PCR); Weiner et al., *Lancet,* 335:1, 1990. HCV replicates largely, if not solely, in the liver and causes both acute and chronic hepatitis.

It is estimated by the Centers for Disease Control and Prevention that HCV is responsible for 160,000 new cases of acute hepatitis in the United States each year. While most patients are asymptomatic, approximately 25% of these patients may develop jaundice or other symptoms of hepatitis, and as many as 70% of these patients may progress to chronic liver disease as evidenced by persistent elevation of serum alanine aminotransferase (ALT) levels as well as continual presence of circulating HCV-RNA. In addition, progression of HCV infection to hepatocellular carcinoma has been well documented; Tong et al., *WJM,* 160.2:133–138, 1994. Epidemiology studies done by the Centers for Disease Control suggest that only 4% of HCV infections are transmitted by blood transfusions, 3% by hemodialysis, 10% by sexual transmission, 35% by intravenous drug use, and in 48% of cases, the mechanism of HCV transmission is unknown.

Interferons are a subclass of cytokines that exhibit both antiviral and antiproliferative activity. On the basis of biochemical and immunological properties, the naturally-occurring human interferons are grouped into three classes: interferon-alpha (leukocyte), interferon-beta (fibroblast) and interferon-gamma (immune). At least fourteen alpha interferons (grouped into subtypes A through H) having distinct amino acid sequences have been identified by isolating and sequencing DNA encoding these polypeptides. Alpha interferons have received considerable attention as potential therapeutic agents due to their antiviral and antitumor growth inhibition.

U.S. Pat. Nos. 4,695,623 and 4,897,471 disclose novel human interferon polypeptides having amino acid sequences which include common or predominant amino acids found at each position among naturally-occurring alpha interferon subtype polypeptides and are referred to as consensus interferons (IFN-con). The IFN-con amino acid sequences disclosed are designated IFN-con$_1$, IFN-con$_2$, and IFN-con$_3$. The preparation of manufactured genes encoding IFN-con and the expression of said genes in *E. coli* are also disclosed. In vitro studies comparing the relative antiviral, antiproliferative, and natural killer cell activities of recombinant IFN-con with either leukocyte or other recombinant type-one interferons demonstrate that IFN-con displays significantly higher activity when compared on a mass basis; Ozes et al., *J Interferon Research,* 12:55–59, 1992.

U.S. Pat. No. 5,372,808 discloses methods of treatment of diseases using consensus interferon. It is shown that IFN-con, when used in the treatment of diseases susceptible to treatment by alpha interferons, does not cause the same degree of side effects in patients as do the alpha interferons. It was further shown that 3 to 5 times higher doses of IFN-con can be used, leading to enhanced therapeutic benefit, with substantially no corresponding increase in the frequency or severity of undesirable side effects.

HCV is one of several clinical indications for which interferons have been approved by the Food and Drug Administration, and IFN-α is currently licensed for use in chronic HCV; Hoofnagle et al., Interferon: Principles and Medical Applications, 1st Edition, Chap. 31, pgs 433–462, 1992. The types of responses that occur during IFN-α therapy can be characterized as: (1) a sustained complete response ("durable"), where patients serum ALT values begin to fall within the first months of treatment, are often normal by two to three months, and remain normal even after therapy is stopped. (these patients may also become negative for serum HCV RNA); (2) a transient complete response followed by relapse when therapy is stopped ("relapse"); (3) a partial or transient response, where patients serum ALT values decrease but do not become normal or become normal transiently and then rise despite continuation of interferon therapy ("partial response"); and (4) no response, where patients serum ALT activities remain elevated during interferon treatment ("non-response").

Use of IFN-α in sufficient dosage to yield clinical efficacy (i.e. at amounts of about $1 \times 10^6$ units/treatment and above) is usually associated with a "flu-like" syndrome characterized by fever, headache, lethargy, arthalgias and myalgias; Tyring et al., Interferon: Principles and Medical Applications, 1st Edition, Section VIII., pgs 399–408, 1992. At higher doses, i.e. $5-10 \times 10^6$ units/treatment and above, other toxicities become more frequent and may be dose-limiting. These effects include nausea, vomiting, diarrhea and anorexia; Id. at 403. Laboratory changes associated with high dose administration include relative leukopenia and thrombocytopenia and serum elevations in liver enzymes; Id.

The recommended IFN-α therapy for chronic HCV is 3–5 MU three times weekly either subcutaneously or intramuscularly for six to twelve months; see e.g., Davis et al., *N Engl J Med.,* 321:1501–1506, 1989; Marcellin et al., *Hepatology,* 13:393–397, 1991; Causse et al., *Gastroenterology,* 101:497–502, 1991; Linsey et al., *Hepatology,* 18:106a, 1993. Generally, approximately fifty percent of IFN-α treated patients demonstrate normal serum ALT levels by the end of therapy. However, following cessation of IFN-α treatment, between 50–100% of the responding patients relapsed, resulting in a 0–25% "durable" ALT response rate, and a 0–25% "relapse" response rate. Unfortunately, there are no reliable means of predicting which patients are likely to respond to IFN-α and which of these will have a "durable" response.

In light of the shortcomings associated with IFN-α treatment of chronic HCV, investigators have set out to increase the response rate in chronic HCV, with several attempts focusing on the use of higher doses. Reports from these studies suggest that higher doses of IFN-α, i.e., between 5 and 10 MU TIW to daily, may increase the long term ALT response rate; see e.g., Linsey et al., *Hepatology,* 18:106a, 1993; Hoofnagle et al., *N Engl J Med.,* 315:1575–1578, 1989; Kakumu et al., Am J Gastroenterology, 85:655–659, 1990. However, because of the accompanying increase in toxicity, these higher doses are difficult to maintain and studies using doses up to 10 MU daily were only performed in patients who were hospitalized for this treatment; Iino et al., *Dig Dis Sci.*, 38:612–618, 1993.

Other attempts have focused on IFN-α retreatment therapy. For example, Toyoda et al., *Amer. Jour. of Gastroent.*, 89:9:1453–1457, 1994, analyzed the retreatment of chronic HCV with IFN-α to get the standpoint for the selection of patients to receive it. Toyoda et al. retreated 23 patients (15 relapses, 8 nonresponses) and reported that eight (34.8%) patients had normalized serum ALT values upon retreatment. All eight patients were patients from the "relapse" group who had had undetectable serum HCV-RNA at the end of their initial IFN-α treatment period. Based on their findings, Toyoda et al. concluded that selection of patients to receive retreatment requires careful consideration of genotype, HCV-RNA concentration, and the clinical response on initial treatment, and that interferon retreatment may be effective in "relapse" cases where the patient has undetectable serum HCV-RNA at the end of initial treatment.

Weiland et al., *Scand J Infect Dis.*, 25:25–30, 1993, report the results of IFN-α retreatment of 10 "relapse" patients (all 10 patients had normalization of serum ALT levels during the nine month initial treatment). Weiland et al. concluded that a 6-month course of retreatment induced a normalization of serum ALT levels once again in most patients (6/10), and that HCV-RNA titers in serum fell to undetectable levels during retreatment, but that all patients relapsed again soon after treatment cessation, i.e., a second course of treatment fails to increase the number of patients with "durable" responses.

Marcellin et al., *J. Infect Dis.*, 167:780, 1993, describe a study to assess the efficacy of retreatment with IFN-α in patients with chronic HCV who did not respond or who relapsed after an initial treatment. In the twelve patients retreated, retreatment with the same dose of the same interferon did not induce any "durable" responses. The overall rate of response to retreatment was not different from that observed with first treatment, i.e., relapsers responded but then relapsed again, and nonresponders to initial treatment were nonresponders to retreatment.

Marriott et al., *J. Infect Dis.*, 166:1200–1201, 1992, evaluated the possible benefit of a second cycle of IFN administration in patients who were "relapse" or "non-response" patients to one cycle of IFN treatment. Of the retreated patients, 70% (14/20) had normalization of serum ALT values during retreatment, with 90% of the "relapse" patients having normalization of serum ALT values, and only 28% of "non-response" patients having normalization during retreatment. Of the 14 patients who normalized during retreatment, only 1 had a "durable" response. Marriott et al. conclude that a second cycle of therapy gave only a transitory benefit and was not useful in improving the rate of "durable" serum ALT normalization.

Schvarcz et al., *Scand J Infect Dis.*, 23:413–420, 1991, report on the outcome of treatment with increased doses of interferon in "non-response" patients. The six "non-response" patients had been treated with 3 MU alpha-2b interferon thrice weekly (t.i.w.), and were retreated with 6 MU t.i.w. for at least 8 weeks. Schvarcz et al. report that none of the "non-response" patients normalized the serum ALT levels during the retreatment with the higher doses. Furthermore, with increased doses, side effects were much more pronounced.

Arase et al., *J. of Gastroent.*, 29:299–304, 1994, studied the outcome of retreatment, using a human lymphoblastoid alpha interferon, of patients who failed to respond to initial interferon beta treatment. Specifically, Arase et al. studied the outcome of retreatment in relation to serum ALT levels after the initial treatment and concluded that high-dose (6 MU) and prolonged readministration of IFN-α may be a worthwhile strategy in patients with HCV subtype III or in those showing transient normalization of serum ALT levels and who are negative for serum HCV-RNA during or after their initial treatment. However, for those with HCV subtype II or persistently positive serum HCV-RNA and abnormal serum ALT levels during and after their initial treatment, retreatment with IFN-α is likely to fail.

Based on the teachings referenced above, it appears that retreatment with IFN-α has limited effectiveness in "relapse" patients, and little, if any, effectiveness in "non-response" patients. More importantly, retreatment fails to be useful in improving the rate of sustained serum ALT normalization, i.e. "durable" responses. It is clear then, that new approaches or modifications to IFN-α therapy of HCV are needed. Therefore, the object of this invention is a method for retreatment, using IFN-con, of patients suffering from HCV, whereby the rate of "durable" responses is increased.

SUMMARY OF THE INVENTION

The invention encompasses methods of retreatment, using a therapeutically effective amount of IFN-con, for patients suffering from HCV who failed to respond to IFN-α therapy, or who, following cessation of IFN-α therapy, suffered relapse. The invention is based on the discovery that retreatment of HCV patients with IFN-con elicits approximately a 46% response rate for relapse and/or nonresponder patients, and that retreatment may be useful in improving the rate of durable ALT normalization.

IFN-con is a nonnaturally-occurring polypeptide having antiproliferative activity. Preferably, IFN-con is a polypeptide having the amino acid sequence of IFN-con$_1$, IFN-con$_2$, or IFN-con3. Most preferably, IFN-con has the amino acid sequence of IFN-con$_1$.

DETAILED DESCRIPTION OF THE INVENTION

As employed herein, human interferon consensus (IFN-con) means a nonnaturally-occurring polypeptide, which predominantly includes those amino acid residues that are common to a subset of IFN-α's representative of the majority of the naturally-occurring human leukocyte interferon subtype sequences and which includes, at one or more of those positions where there is no amino acid common to all subtypes, an amino acid which predominantly occurs at that position and in no event includes any amino acid residue which is not extant in that position in at least one naturally-occurring subtype. IFN-con encompasses but is not limited to the amino acid sequences designated IFN-con$_1$, IFN-con$_2$ and IFN-con$_3$ which are disclosed in commonly owned U.S. Pat. Nos. 4,695,623 and 4,897,471, the entire disclosures of which are hereby incorporated by reference. DNA sequences encoding IFN-con may be synthesized as described in the above-mentioned patents or other standard methods.

IFN-con polypeptides are preferably the products of expression of manufactured DNA sequences transformed or transfected into bacterial hosts, especially *E. coli*. That is, IFN-con is recombinant IFN-con. IFN-con is preferably produced in *E. coli* and is purified by procedures known to those skilled in the art and generally described in Klein et al., *J. Chromatog.* 454:205–215 (1988). IFN-con$_1$ purified in this manner is reported to have a specific activity of $3 \times 10^9$ units/mg protein as measured in the cytopathic effect inhibition assay using the T98G human cell line; Fish et al. *J. Interferon Res.* 9, 97–114 (1989).

The subject invention provides for a method of retreating, using a therapeutically effective amount of IFN-con, a patient suffering from HCV, who had previously failed to respond to IFN-α therapy or had previously responded to IFN-α therapy, but, upon cessation of therapy, suffered relapse. A preferred embodiment of the invention is a method of retreatment involving administering a therapeutically effective amount of IFN-con$_1$, IFN-con$_2$, or IFN-con$_3$. More preferably, a therapeutically effective amount of IFN-con$_1$ is administered. Most preferably 15 MU IFN-con$_1$ is administered subcutaneously 3 times weekly for 24 or 48 weeks.

In Example 1 provided below, it is shown that IFN-con$_1$ is effective in eliciting approximately a 46% response in patients who had previously failed to respond to IFN therapy, or who, upon cessation of IFN therapy, suffered relapse. More importantly, it is shown that 27% of the retreated patients have a "durable" response. The example is offered to more fully illustrate the invention but is not to be construed as limiting the scope thereof.

EXAMPLE 1

Efficacy of IFN-con$_1$ Administered to Patients with HCV After Prior Treatment with Interferon A randomized, open-label, multicenter study was undertaken to determine the efficacy of retreatment with IFN-con$_1$ in patients with HCV who exhibit serum ALT values above the upper limit of normal after previous treatment with interferon, i.e. "relapse" or "non-response" patients. Efficacy of IFN-con$_1$ was evaluated by measuring changes in serum ALT values during the course of retreatment. In addition, the study demonstrates the durability of response and the effects of IFN-con$_1$ retreatment on serum HCV RNA as measured by PCR analysis. The study was divided into two independent concurrent Cohorts: Cohort A (retreatment) and Cohort B (observation only).

A. Product Description

IFN-con$_1$ was produced in *E. coli* using methods described in U.S. Pat. Nos. 4,695,623 and 4,897,471. IFN-con$_1$ was purified by procedures generally described in Klein et al., supra (1988). For subcutaneous administration in the current study, IFN-con$_1$ was supplied as a clear, colorless, sterile protein solution free of particulates and formulated in an aqueous buffer before undergoing sterile filtration and filling the vials. Recombinant IFN-con$_1$ is not less than 95% pure.

B. Patient Selection

The study included approximately 431 patients who had completed Amgen Inc. protocol CIFN-9210. CIFN-9210 was a double-blind, randomized, positive-controlled, multicenter study to determine the efficacy of IFN-con$_1$ administration at two dose levels, 3 µg (3 MU) and 9 µg (9 MU) as compared to 15 µg (3 MU) Intron® A (Schering-Plough). Durability of response, pre- and post-treatment intra-patient changes in serum HCV RNA, liver histology, formation of antibody to interferon, and quality of life were compared.

To be eligible for CIFN-9210, patients had to be at least 18 years old with chronic HCV, positive for HCV RNA, with adequate bone marrow and organ function, and with ALT greater than 1.5 times the upper limit of normal. Eligible patients were randomly assigned to receive subcutaneous injections of 3 µg IFN-con$_1$, 9 µg IFN-con$_1$, or 15 µg Intron® A three times weekly for 24 weeks. Patients were then observed for 24 weeks.

Efficacy response criteria for ALT were as follows: (1) a complete response (ALT-CR) was defined as a decrease in the monthly ALT values to less than or equal to the upper limit of normal any time during the double-blind treatment period that remains less than or equal to the upper limit of normal at the end of the double-blind treatment period; (2) a near-complete response (ALT-NCR) was defined as any decrease in the monthly ALT value to less than or equal to 1.5 times the upper limit of normal any time during the double-blind treatment period that remains less than or equal to 1.5 times the upper limit of normal at the end of the double-blind treatment period; (3) a partial response (ALT-PR) was defined as a decrease in ALT value to less than or equal to 50% of baseline but not less than or equal to 1.5 times the upper limit of normal any time during the double-blind treatment period. The decrease must remain less than or equal to 50% of baseline but not less than or equal to 1.5 times the upper limit of normal at the end of the double-blind treatment period to be classified as an ALT-PR; and (4) any response not meeting the criteria specified above was considered a non-response (ALT-NR).

Efficacy was assessed in patients who had serum ALT values above the upper limit of normal at the end of the 24-week post-treatment observation period in protocol CIFN-9210, and in patients whose serum ALT values were within normal limits at completion of protocol CIFN-9210 and subsequently increased above the upper limit of normal within approximately four years after completing protocol CIFN-9210.

C. Retreatment Procedures

Treatment Cohort A

Eligible patients were enrolled within approximately 28 days of completing protocol CIFN-9210. Patients who had serum ALT values above the upper limit of normal for two consecutive measurements at least two weeks apart were enrolled and randomized to receive treatment with 15 µg of IFN-con$_1$ in a 1:1 ratio for either 24 weeks or 48 weeks. Study drug was administered subcutaneously three times weekly at least 48 hours apart. Patients were monitored for safety, efficacy, and tolerability of study drug throughout the study. Response at the end of the 24- or 48-week treatment period and at the end of the 24-week post-treatment observation period was determined.

Patients who did not show a reduction in serum ALT values to less than 1.5 times the upper limit of normal or at least a 50% reduction from their baseline value at study entry within three months of starting retreatment were withdrawn from the study. Furthermore, for patients randomized to 48 weeks of retreatment, if, in the opinion of the investigator, no additional benefit was seen by week 24, some of these patients were withdrawn from study.

Patients who experienced an intolerable Grade 2 toxicity, Grade 3 toxicity, or Grade 4 neutropenia (criteria established by the World Health Organization and described further in Miller et al., *Cancer* 47: 210–211, 1981) that was judged by the Investigator to be possibly, probably or definitely related to study drug had their dose of study drug withheld until the toxicity was judged by the Investigator to be a tolerable Grade 2 toxicity or less. Study drug was restarted at the next lower dose as shown in Table 1.

TABLE 1

Dose Reductions Due to Toxicity

| Toxicity** | Dose (μg) IFN-con$_1$ | Injection Volume (mL) |
|---|---|---|
| None | 15 | 0.5 |
| First | 12 | 0.4 |
| Second | 9 | 0.3 |
| Third | 6 | 0.2 |
| Fourth | 3 | 0.1 |

**Patients who experienced more than four dose reductions were withdrawn from study.

Patients were withdrawn from study if they required more than four dose reductions, or if they experienced an intolerable Grade 2 toxicity, or Grade 3 toxicity (excluding neutropenia) thought to be related to study drug for greater than 14 days. Patients who experienced a Grade 4 toxicity (excluding neutropenia) were also withdrawn. Patients who completed the 24- or 48-week retreatment period will continue on to a post-treatment observation period for up to an additional four years.

Treatment Cohort B

Patients whose serum ALT values were less than or equal to the upper limit of normal within 28 days after the completion of protocol CIFN-9210 (week 60) were enrolled into Cohort B and followed for durability of response (time period in which serum ALT values remain within the normal range) and time to relapse (time point in which serum ALT values increase above the upper limit of normal) for up to four years. At the time of relapse, these patients will be given a new randomization number and assigned to a Cohort A retreatment group as described above.

D. Results

TABLE 2

Percentage of Patients with Normal ALT Values After Retreatment with 15 μg a IFN-Con$_1$

| Initial Treatment Group* | Treatment Period Week 24 |
|---|---|
| Intron ® A (15 μg) | 43% (28/65) |
| IFN-Con$_1$ (3 μg) | 42% (25/59) |
| IFN-Con$_1$ (9 μg) | 54% (26/48) |

*this represents the type and dose of interferon used to treat the group initially As illustrated by Table 2 above, patients retreated with IFN-con$_1$ at 15 μg three times weekly for 24 weeks had complete ALT response rates that ranged from 42% to 54%. The above demonstrates that retreatment with IFN-con$_1$ is effective in eliciting a complete response in patients who had previously failed to respond to interferon therapy, or who, upon cessation of therapy, suffered relapse.

TABLE 3

Percentage of Patients with "Durable" Responses After Retreatment with 15 μg IFN-Con$_1$

| Initial Treatment Group* | Period After Treatment Stopped Week 12 |
|---|---|
| Intron ® A (15 μg) | 25% (16/65) |
| IFN-Con$_1$ (3 μg) | 25% (15/59) |
| IFN-Con$_1$ (9 μg) | 33% (16/48) |

*this represents the type and dose of interferon used to treat the group initially As illustrated by Table 3 above, retreatment with IFN-con$_1$ at 15 μg three times weekly for 24 weeks resulted in a "durable" response rate that ranged from 25% to 33%. This data demonstrates that retreatment with IFN-con$_1$ increases the "durable" response rate in chronic HCV patients as compared to previously reported treatment and/or retreatment regimens.

While the present invention has been described in terms of the preferred embodiments, it is understood that variations and modifications will occur to those skilled in the art. Therefore, it is intended that the appended claims cover all such equivalent variations which come within the scope of the invention as claimed.

What is claimed is:

1. A method for retreating HCV patients, said patients having failed to respond to previous treatment with an interferon, comprising administering to a patient a therapeutically effective amount of interferon consensus.

2. A method according to claim 1, wherein said interferon consensus is selected from the group consisting of IFN-con$_1$, IFN-con$_2$, and IFN-con$_3$.

3. A method according to claim 2, wherein said interferon consensus is IFN-con$_1$.

4. A method according to claim 1 wherein said interferon consensus is a product of prokaryotic expression of an exogenous DNA sequence.

5. A method according to claim 1, wherein the therapeutically effective amount is administered orally, intravenously, intramuscularly, subcutaneously, intranasally, or intralesionally.

6. A method according to claim 1, wherein the therapeutically effective amount is 15 μg administered subcutaneously three times weekly for 24 weeks.

7. A method for obtaining normalized serum alanine aminotransferase (ALT) levels in a patient suffering from HCV and having failed to respond to previous treatment with interferon therapy, comprising administering to said patient a therapeutically effective amount of interferon consensus.

* * * * *